United States Patent
Zhang et al.

(10) Patent No.: US 8,618,308 B2
(45) Date of Patent: Dec. 31, 2013

(54) PROCESS FOR THE PREPARATION OF 4-(1-HYDROXY-1-METHYLETHYL)-2-PROPYL-IMIDAZOLE-5-CARBOXYLATES

(75) Inventors: Fuli Zhang, Shanghai (CN); Taizhi Wu, Shanghai (CN); Meihua Xie, Shanghai (CN)

(73) Assignee: Shanghai Institute of Pharmaceutical Industry, Shanghai (CN)

( * ) Notice: Subject to any disclaimer, the term of this patent is extended or adjusted under 35 U.S.C. 154(b) by 0 days.

(21) Appl. No.: 13/129,686

(22) PCT Filed: Nov. 17, 2008

(86) PCT No.: PCT/CN2008/073081
§ 371 (c)(1), (2), (4) Date: Sep. 8, 2011

(87) PCT Pub. No.: WO2010/054515
PCT Pub. Date: May 20, 2010

(65) Prior Publication Data
US 2012/0095237 A1    Apr. 19, 2012

(51) Int. Cl.
*C07D 233/64*    (2006.01)

(52) U.S. Cl.
USPC ...................................................... 548/334.5

(58) Field of Classification Search
USPC ...................................................... 548/334.5
See application file for complete search history.

(56) References Cited

U.S. PATENT DOCUMENTS

2006/0258727 A1    11/2006    Hedvati et al.

FOREIGN PATENT DOCUMENTS

| CN | 1189490 A | 8/1998 |
| CN | 1467209 A | 1/2004 |
| CN | 101311168 A | 11/2008 |

OTHER PUBLICATIONS

Hiroaki Yanagisawa, "Nonpeptide Angiotensin II Receptor Antagonists: Synthesis, Biological Activities, and Structure-Activity Relationships of Imidazole-5-carboxylic Acids Bearing Alkyl, Alkenyl and Hydroxyalkyl Substituents at the 4-Position and Their Related Compounds," J. Med. Chem. 1996, 39(a), pp. 323-338, ISSN: 0022-2623.
International Search Report PCT/CN2008/073081, 2 pages.
WuTai-Zhi, "A Novel Synthesis of Olmesartan Medoxomil and Examination of Its Related Impurities", Acta Pharmaceutica Sinica 2006, 41(6), pp. 537-543.

*Primary Examiner* — Yong Chu
*Assistant Examiner* — Sonya Wright
(74) *Attorney, Agent, or Firm* — Lihua Zheng; Mary S. Consalvi; Proskauer Rose LLP

(57) ABSTRACT

The present invention discloses a process for obtaining 4-(1-hydroxy-1-methylethyl)-2-propyl-imidazole-5-carboxylate by the reaction of 4,4-dimethyl-2-propyl-4,6-dihydrofuro[3,4-d]imidazole, or its hydrolysis product, or its ring-opening product, with alcohol under appropriate catalytic conditions. Furthermore, the present invention also provides a process for obtaining high purity 4,4-dimethyl-2-propyl-4,6-dihydrofuro[3,4-d]imidazole.

12 Claims, No Drawings

PROCESS FOR THE PREPARATION OF 4-(1-HYDROXY-1-METHYLETHYL)-2-PROPYL-IMIDAZOLE-5-CARBOXYLATES

CROSS-REFERENCE TO RELATED APPLICATIONS

This application is a National Phase Application of International Application No. PCT/CN2008/073081, filed on Nov. 17, 2008. The disclosure of the above application is incorporated herein by reference in its entirety.

FIELD OF INVENTION

The present invention relates to the field of pharmaceutical synthesis, particularly, to the preparation of high purity 4-(1-hydroxy-1-methylethyl)-2-propyl-imidazole-5-carboxylate.

BACKGROUND OF THE INVENTION

Ethyl 4-(1-hydroxy-1-methylethyl)-2-propyl-imidazole-5-carboxylate (formula V) is a key intermediate for the synthesis of olmesartan medoxomil, which can be produced via the reaction of diethyl 2-propyl-imidazole-4,5-dicarboxylate, the raw material, with methylmagnesium bromide, followed by the acidification with saturated ammonium chloride solution (J. Med. Chem. 1996, 39, 323-338).

Moreover, hydroxyl methylated product of olmesartan medoxomil (impurity 1), and hydroxyl eliminated product of olmesartan medoxomil (impurities 2) are the two major impurities in the olmesartan medoxomil as reported by Hedvati Lilach in US2006258727 on Nov. 16, 2006.

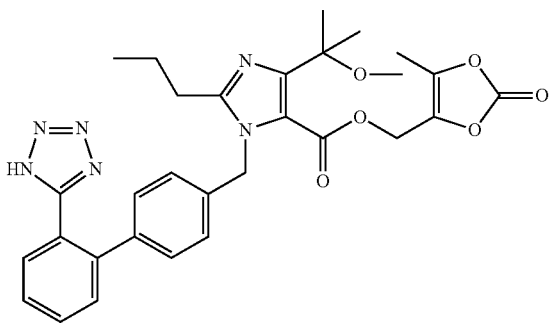

Impurity 1

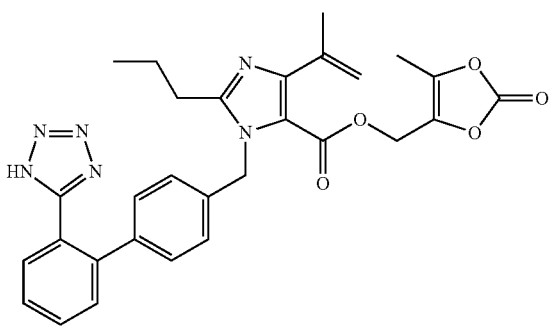

Impurity 2

The major causes for the formation of impurity 1 and impurity 2 in olmesartan medoxomil are also disclosed by Hedvati Lilach, which are, the reaction of the compound of formula IV with methylmagnesium bromide produces not only the main product as shown by formula V, but also the hydroxyl methylated product (impurity 3) and the hydroxyl eliminated product (impurity 4), compound of formula V containing impurity 3 and impurity 4 will lead to the olmesartan medoxomil containing impurities 1 and 2 after following reactions.

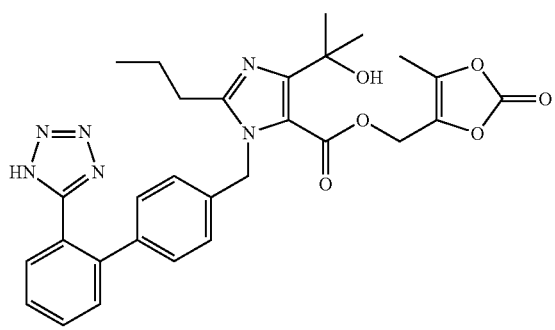

Olmesartan Medoxomil

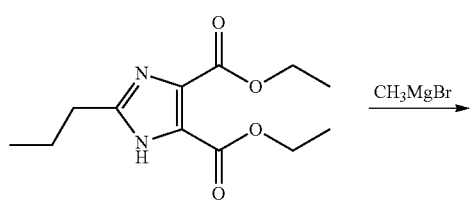

Formula IV

-continued

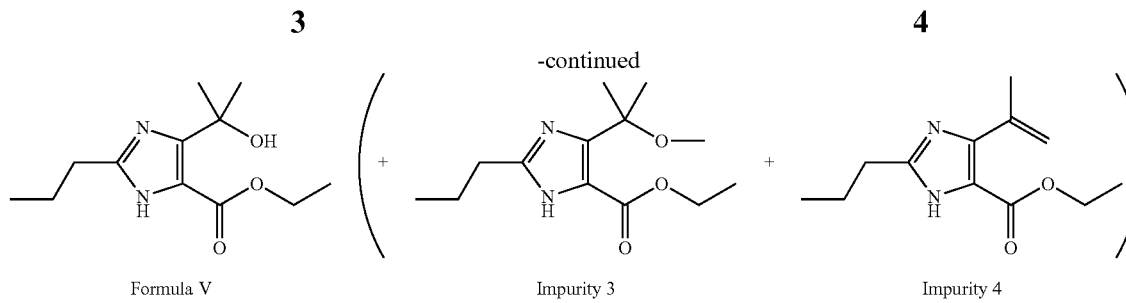

Formula V          Impurity 3          Impurity 4

Therefore, there is an urgent need in the art for a novel and more effective process for the preparation of ethyl 4-(1-hydroxy-1-methylethyl)-2-propyl-imidazole-5-carboxylate (formula V), furthermore, high purity ethyl 4-(1-hydroxy-1-methylethyl-2-propyl-imidazole-5-carboxylate (formula V) can be obtained by the provided process so that high purity olmesartan medoxomil can be produced.

SUMMARY OF THE INVENTION

One object of the present invention is to provide a process to obtain 4-(1-hydroxy-1-methylethyl)-2-propyl-imidazole-5-carboxylate (formula I).

Another object of the present invention is to provide a process to obtain high purity 4-(1-hydroxy-1-methylethyl)-2-propyl-imidazole-5-carboxylate (formula I).

According to the first aspect, the present invention provides a process for the preparation of compound of formula I, comprising mixing the compound of formula II, or its hydrolysis product, or its ring-opening product, with alcohol R—OH to produce compound of formula I,

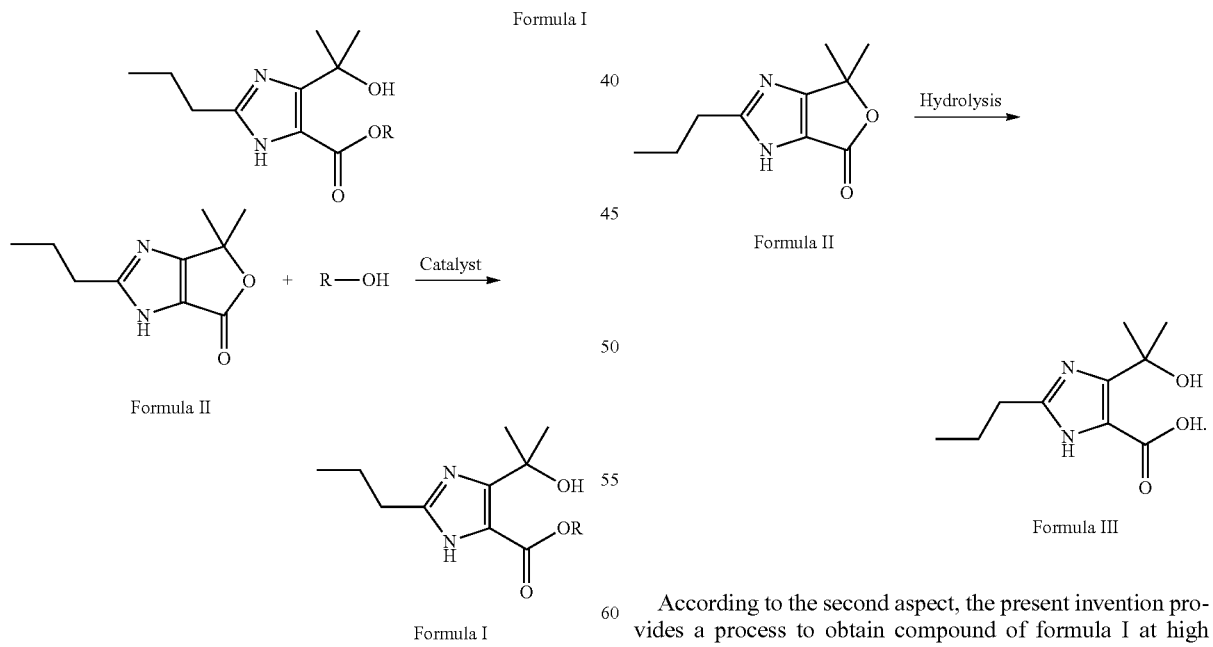

Formula I

Formula II

Formula I wherein R is selected from $C_1$-$C_6$ alkyl.

In another preferred embodiment, the hydrolysis product or ring-opening product is selected from a compound of formula III.

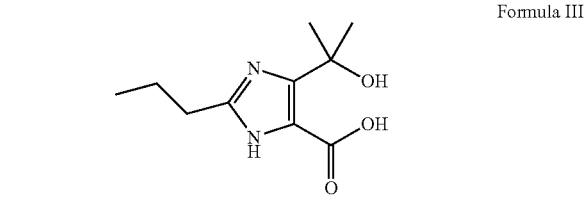

Formula III

In another preferred embodiment, the catalyst is a catalyst for transesterification or a condensation agent for oxygen acylation.

In another preferred embodiment, the reaction temperature is in the range of −20° C. to the reflux temperature of the alcohol R—OH.

In another preferred embodiment, the reaction time is between 30 minutes and 72 hours.

In another preferred embodiment, R is selected from $C_1$ to $C_3$ alkyl.

In another preferred embodiment, the compound of formula III is generated by

Formula II

Hydrolysis

Formula III

According to the second aspect, the present invention provides a process to obtain compound of formula I at high purity, comprising the following steps prior to the aforementioned step for producing compound of formula I:

(1) hydrolyzing compound of formula V containing impurities 3 and/or 4 to obtain compound of formula III, while said impurities 3 and/or 4 being hydrolyzed into impurities 5 and/or 6;

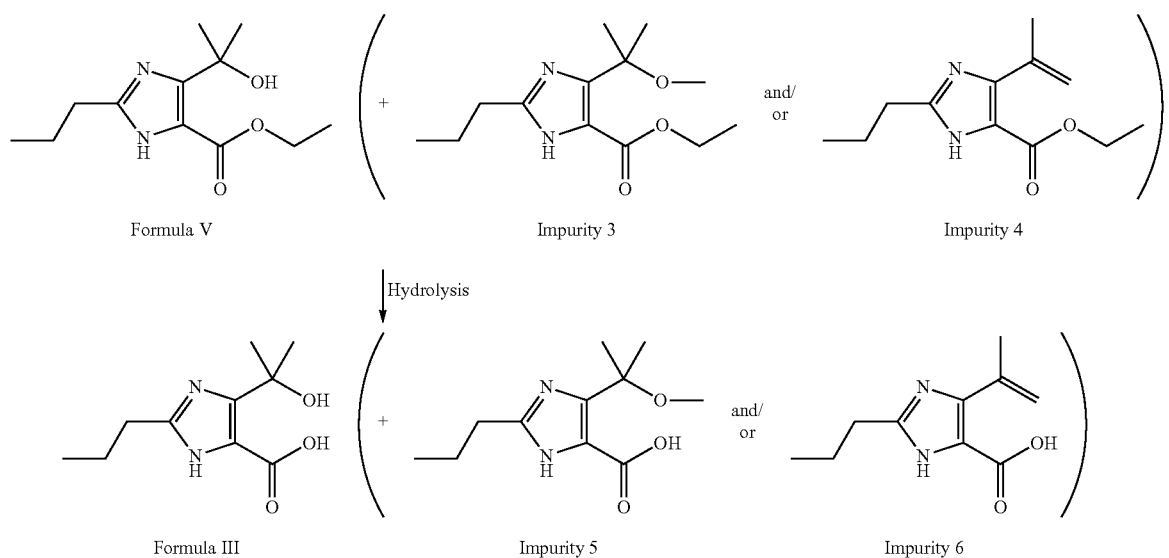

(2) mixing the compound of formula III with a condensation agent in solvent to produce compound of formula II;

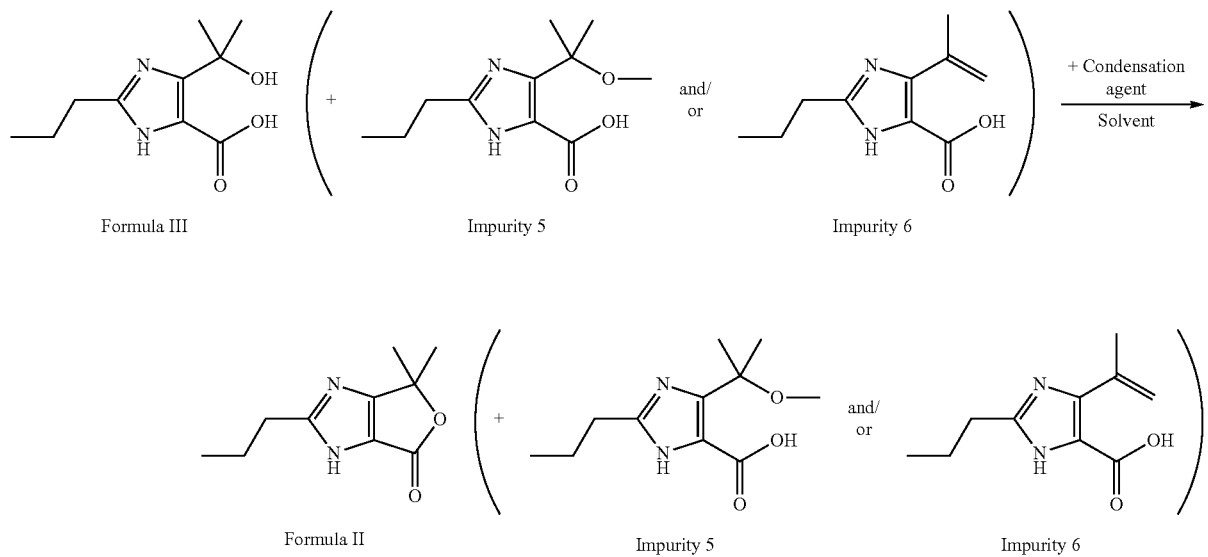

(3) mixing the compound of formula II with organic solvent and alkaline aqueous solution to remove salt of impurity 5 and/or salt of impurity 6 from the aqueous layer and collecting compound of formula II in the organic layer,

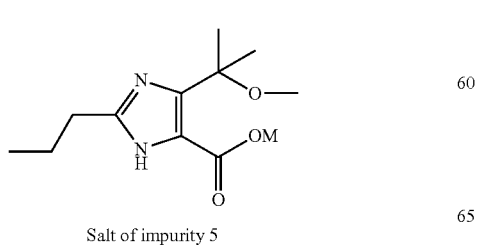

Salt of impurity 5

-continued

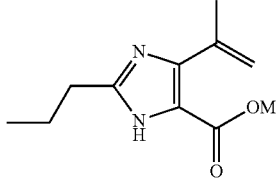

Salt of impurity 6 wherein M represents a group which can form water-soluble salt with carboxyl group, preferably alkali metal.

In another preferred embodiment, said step (3) is followed by the following steps:

(3') extracting the aqueous layer for 1-5 times with organic solvent; and/or (3") washing the organic layer with saturated saline solution for 1-5 times.

In another preferred embodiment, the extraction or washing are performed 1-3 times.

In another preferred embodiment, said step (3) is followed by the following steps: drying, filtration of the organic layer, distillation to remove the solvent, and recrystallization, to obtain compound of formula II.

In another preferred embodiment, said organic solvent can be selected from hydrocarbons, halohydrocarbons, ethers, and esters with no particular requirement providing that compound of formula II can be dissolved in the solvent and aqueous layer can be separated.

In another preferred embodiment, said condensation agent used in step (2) includes condensation agents capable of catalyzing esterifications or oxygen acylations, or dehydrants for esterifications.

In another preferred embodiment, said step (2) is performed at reaction temperature in the range of −20 to 100° C., reaction time in the range of 1 to 56 hours.

Therefore, the present invention provides a novel and more effective process for the preparation of ethyl 4-(1-hydroxy-1-methylethyl)-2-propyl-imidazole-5-carboxylate (formula V), the provided process can further produce ethyl 4-(1-hydroxy-1-methylethyl)-2-propylimidazole-5-carboxylate (formula V) at high purity so that high purity olmesartan medoxomil can be obtained.

DETAILED DESCRIPTION OF THE EMBODIMENTS

After extensive and intensive studies, the inventors found that compound of formula I can be produced by the reaction of compound of formula II, or its hydrolysis product, or its ring-opening product, with alcohol under appropriate catalytic conditions.

Furthermore, the inventors also found that:

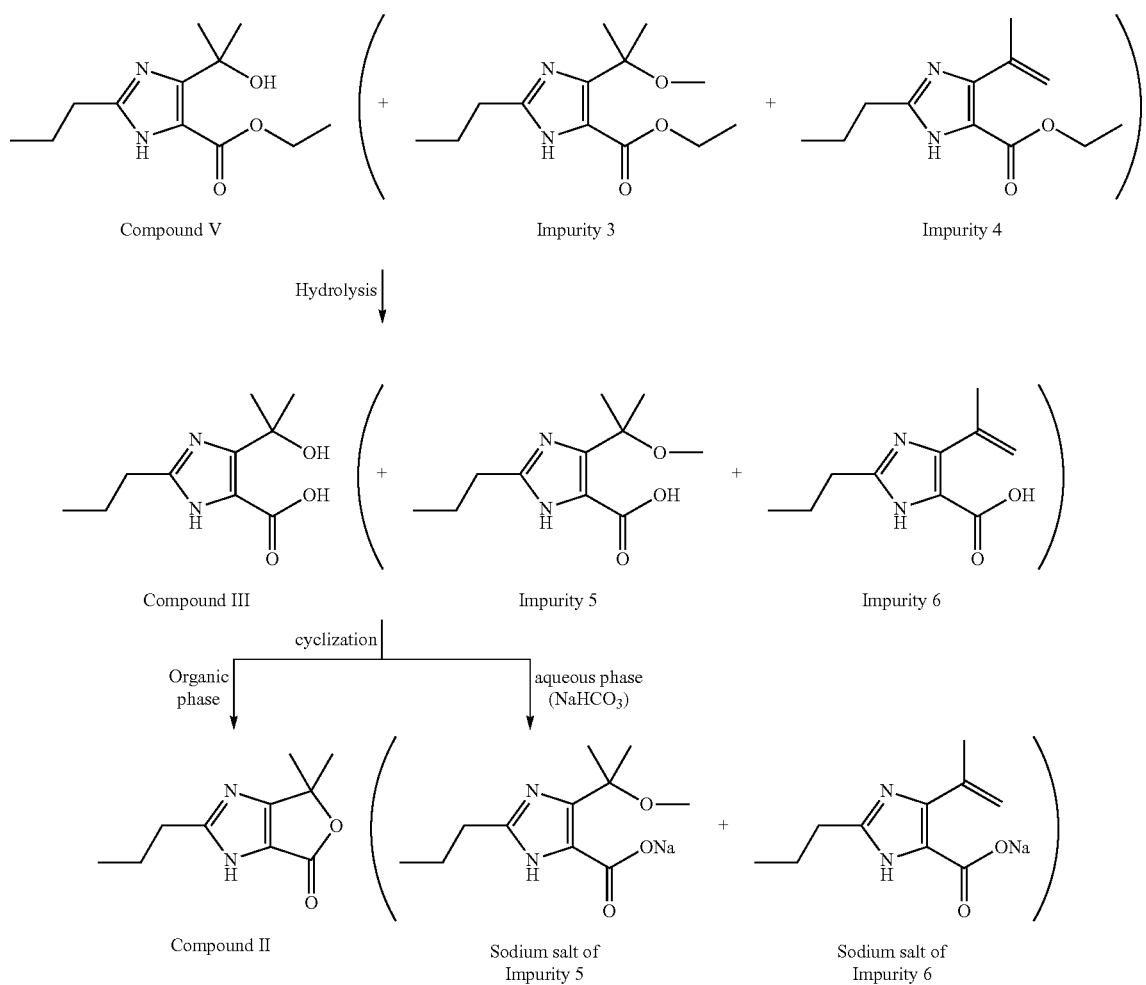

The raw material, compound of formula V, is hydrolyzed into compound of formula III, which is converted to compound of formula II via intramolecular cyclization, while impurities 3 and/or 4 in compound of formula V will be hydrolyzed into impurities 5 and/or 6; once the lactone compound of formula II is produced via the intramolecular cyclization of compound of formula III, the compound of formula II containing impurities 5 and/or 6 is dissolved in organic solvents (such as ethyl acetate), and washed with alkaline aqueous solution (such as saturated sodium bicarbonate solution) in order to remove impurities 5 and/or 6, and to obtain high purity compound of formula II, therefore, compound of formula I is produced at high purity.

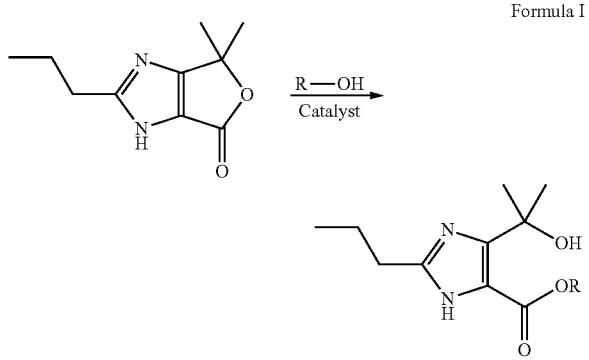

Formula I

Compound of formula II, its hydrolysis product, or its ring-opening product wherein R is selected from $C_1$-$C_6$ alkyl.

As described herein, compound of formula I is 4-(1-hydroxy-1-methylethyl)-2-propylimidazole-5-carboxylate, compound of formula II is 4,4-dimethyl-2-propyl-4,6-dihydrofuro[3,4-d]imidazole, compound of formula III is 4-(1-hydroxy-1-methylethyl)-2-propyl-imidazole-5-carboxylic acid, compound of formula IV is diethyl 2-propylimidazole-4,5-dicarboxylate, compound of formula V is ethyl 4-(1-hydroxy-1-methylethyl)-2-propyl-imidazole-5-carboxylate.

The process according to the present invention is mixing compound of formula II, or its hydrolysis product, or its ring-opening product with alcohol R—OH to produce compound of formula I. In a preferred embodiment according to the present invention, compound of formula II is hydrolyzed into compound of formula III, which is then mixed with alcohol R—OH to produce compound of formula I.

According to the present invention, there is no particular limitation on the catalyst for transesterification providing that it is capable of catalyzing transesterification, it can be inorganic acid selected from hydrochloric acid, hydrogen chloride gas, sulfuric acid, phosphoric acid, hydrobromic acid, hydrogen bromide gas, hydroiodic acid; and organic acid selected from trifluoromethanesulfonic acid, p-toluenesulfonic acid, rare-earth metal salts of trifluorosulfonic acid, strong acid ion exchange resin, and super acid.

The hydrolysis catalyst according to the present invention for hydrolyzing compound of formula II into compound of formula III is well known in the art. Any catalyst capable of catalyzing the hydrolysis reaction, such as alkali metal hydroxide: lithium hydroxide, sodium hydroxide or potassium hydroxide, can be used.

The esterification of compound of formula III in alcohol (R—OH) for producing compound of formula II according to the present invention can use catalyst well-known in the art. Catalysts for esterification or condensation agents for oxygen acylation are all applicable for catalyzing this reaction, for example, inorganic acid selected from hydrochloric acid, hydrogen chloride gas, sulfuric acid, phosphoric acid, hydrobromic acid, hydrogen bromide gas, hydroiodic acid, and organic acid selected from trifluoromethanesulfonic acid, p-toluenesulfonic acid, rare-earth metal salts of trifluorosulfonic acid, strong acid ion exchange resin, super acid, and thionyl chloride.

For the process according to the present invention, the reaction temperature is between −20° C. to reflux temperature of the solvent, preferably between room temperature to reflux temperature of the solvent; reaction time allows the reaction to complete, which is generally between 30 minutes to 72 hours, preferably between 30 minutes to 48 hours.

R of the alcohol (R—OH) is selected from $C_1$-$C_6$ alkyl, preferably ethanol.

Furthermore, according to the present invention, compound of formula II without or with little impurities 5 and/or 6 can be obtained and subjected to transesterification reaction with alcohol (R—OH) to produce compound of formula I, or compound of formula II can be hydrolyzed into compound of formula III, which is then esterified in alcohol (R—OH) to produce compound of formula I. The compound of formula I is produced with little impurities.

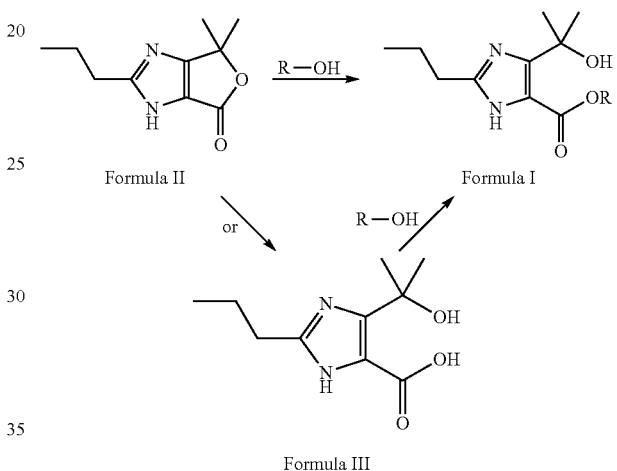

According to a preferred embodiment of the present invention, ethyl 4-(1-hydroxy-1-methylethyl)-2-propyl-imidazole-5-carboxylate is produced by transesterification reaction in ethanol, or compound of formula III produced by hydrolysis of compound of formula II is esterified in ethanol to produce ethyl 4-(1-hydroxy-1-methylethyl)-2-propyl-imidazole-5-carboxylate (formula V). Using this high purity compound of formula V, olmesartan medoxomil with low impurity content can be produced by subsequent reaction and simple purification.

Salt of impurity 5 or salt of impurity 6 can also be reutilized by techniques well known in the art.

According to one preferred embodiment of in the present invention, the process of preparation comprises the following steps:

(1) reacting compound of formula IV with methylmagnesium bromide to produce compound of formula V;

(2) hydrolyzing compound of formula V into compound of formula III;

(3) mixing compound of formula III with condensation agent in solvent to obtain compound of formula II;

(4) mixing compound of formula II with organic solvent and alkaline aqueous solution to obtain compound of formula II from the organic layer;

(5) mixing the obtained compound of formula II with alcohol R—OH to produce compound of formula I, or hydrolyzing compound of formula II into compound of formula III, which is then mixed with alcohol R—OH to produce compound of formula I.

The reaction condition for step (1) can be routinely determined in the art, for example, the reaction with methylmagnesium bromide can be conducted in ether solvent, then the reactant can be acidified and the product can be extracted.

The hydrolysis in step (2) can be customary in the art providing that the ester hydrolysis can be accomplished. For example, sodium hydroxide solution is added into dissolved compound of formula V and the mixture is refluxed and hydrolyzed.

Step (3) is generally conducted in organic solvent. Conventional solvent in the art can be used provided that there is no adverse effect on the reaction or the reagents used, and the reactant can be dissolved or dissolved to some extent in the solvent. Suitable solvents include, but not limited to, hydrocarbons, ethers, ketones, sulfoxides, amides, pyridines or cyanides. Suitable hydrocarbons include, but not limited to, alkanes, halohydrocarbons, benzene, toluene or xylene. Suitable ethers include, but not limited to, ethyl ether, propyl ether, tetrahydrofuran or dioxane. Suitable ketones include, but not limited to, acetone or methyl ethyl ketone. Suitable sulfoxides include, but not limited to, dimethyl sulfoxide. Suitable amides include, but not limited to, N,N-dimethylformamide, N,N-diethyl formamide or N,N-dimethylacetamide.

The condensation agent used in step (3) can be any customary condensation agent in the art which is capable of catalyzing esterification or oxygen acylation. Dehydrants for esterification may be used as well. The 5-carboxyl can form active ester or acid anhydride prior to the condensation with the hydroxyl in the 1-hydroxy-1-methylethyl on position 4 to form lactone. Preferred reagents include inorganic acids, carbodiimides, acids and acid anhydrides or thionyl chloride. Suitable inorganic acids include, but not limited to, hydrochloric acid, hydrobromic acid, sulfuric acid or phosphoric acid. Suitable carbodiimides include, but not limited to, dicyclohexylcarbodiimide. Suitable acids and acid anhydrides include, but not limited to, trifluoroacetic acid or trifluoroacetic anhydride.

Step (3) imposes no particular limitation on reaction temperature, which is generally in the range of −20 to 100° C., preferably 0 to 50° C. Reaction time will depend on the solvent and reaction temperature; usually it is in the range of 1 to 56 hours.

The organic solvent in step (4) can be selected from hydrocarbons, preferably toluene, para-xylene; halohydrocarbons, preferably dichloromethane, 1,2-dichloroethane, chloroform; ethers, preferably isopropyl ether, tetrahydrofuran, dioxane, methyl tert-ether; and esters, preferably ethyl acetate, butyl acetate.

The alkaline aqueous solution in step (4) can be routine alkaline aqueous solution in the art, suitable alkali include, but not limited to, alkali metal hydroxides, alkali metal carbonates, alkali metal bicarbonates and organic bases, preferably alkali metal bicarbonates, and alkali metal carbonates. There is no particular limitation on concentration of alkaline aqueous solution, saturated solution is preferred.

One preferred approach for step (4) is thorough mixing of compound of formula II with organic solvents so that the compound is completely dissolved, followed by fully mixing with the alkaline aqueous solution and separating the organic layer. Preferably, after the organic layer is separated, the aqueous layer is further extracted for 1-5 times, 1-3 times preferred, with organic solvent, all the organic layers are then combined and washed with saturated saline solution for 1-5 times, 1-3 times preferred.

The aforementioned features of the present invention or the characteristics provided in examples can be combined as appropriate.

The main advantages of this invention are:
1. the present invention provides a simple and cost-effective process for the preparation of compound of formula I;
2. the long plagued problem in the art regarding difficulties in impurity removal of ethyl 4-(1-hydroxy-1-methylethyl)-2-propylimidazole-5-carboxylate (formula V), the intermediate for olmesartan medoxomil synthesis, is well solved.

Details of the present invention are set forth in the examples and description below. It is understood that the following examples are offered by way of illustration and are not intended to limit the scope of the invention. The unspecified conditions of the experimental methods in the following examples can be determined in accordance with routine conditions or according to manufacturer's recommendation. Unless otherwise indicated, the percentage and number of parts are all by weight.

Unless defined otherwise, technical and scientific terms used herein have the same meaning as is commonly understood by one skilled in the art. Moreover, any methods and materials similar or equivalent to those described herein can also be used in the practice of the present invention. Preferred methods and materials described herein are for demonstration purposes only.

Example 1

Purification of 4,4-dimethyl-2-propyl-4,6-dihydrofuro[3,4-d]imidazole (formula II)

3.0 grams of 4,4-dimethyl-2-propyl-4,6-dihydrofuro[3,4-d]imidazole (formula II) and 30 ml of ethyl acetate were added into 100 ml three-necked flask and stirred until completely dissolved. 30 ml of saturated sodium bicarbonate solution was added and stirred for 30 minutes. The organic layer was separated and the aqueous layer was further extracted with 10 ml×3 of ethyl acetate. The organic portion was washed once with 30 ml saturated saline solution, dried over anhydrous magnesium sulfate and filtered, the solvent was evaporated to give 3.0 grams of compound of formula II, resulting in a yield of 97%.

Example 2

The preparation of ethyl 4-(1-hydroxy-1-methylethyl)-2-propyl-imidazole-5-carboxylate (formula I, wherein R is ethyl)

3.0 grams of 4,4-dimethyl-2-propyl-4,6-dihydrofuro[3,4-d]imidazole (formula II) from Example 1 and 30 ml of ethanol were added into 100 ml three-necked flask and stirred until completely dissolved. Anhydrous hydrogen chloride gas was supplied while the temperature was maintained at 10-20° C. until the reaction completed. The reaction mixture was then allowed to cool to ambient temperature, the solvent was evaporated, 30 ml of ethyl acetate and 30 ml of water were added, and the mixture was adjusted to basic using sodium bicarbonate. The organic layer was separated and the aqueous layer was further extracted with 10 ml×3 of ethyl acetate. The organic portion was washed once with saturated saline solution, dried over anhydrous magnesium sulfate and filtered, the solvent was evaporated to give 2.8 grams of ethyl 4-(1-hydroxy-1-methylethyl)-2-propyl-imidazole-5-carboxylate, resulting in a yield of 75%.

$^1$H NMR (CDCl$_3$ 400 MHz): δ10.4-8.9 (1H, broad peak, disappeared after heavy water exchange), 5.99 (1H, singlet peak, disappeared after heavy water exchange), 4.34 (2H, quartet peak), 2.66 (2H, triplet peak), 1.75 (2H, multiplet peak), 1.62 (6H, singlet peak), 1.31 (3H, triplet peak), 0.94 (3H, triplet peak); MS (Q-Tof micro, ESI$^+$): 241.10 (M+1)

Example 3

The preparation of ethyl 4-(1-hydroxy-1-methylethyl)-2-propyl-imidazole-5-carboxylate (formula I, wherein R is ethyl)

3.0 grams of 4,4-dimethyl-2-propyl-4,6-dihydrofuro[3,4-d]imidazole (formula II) from Example 1, 30 ml of ethanol and 0.1 ml of concentrated sulfuric acid were added into 100 ml three-necked flask and stirred until completely dissolved, heated to 40~50° C. and maintained at that temperature until the reaction completed. The reaction mixture was then allowed to cool to ambient temperature, the solvent was evaporated, 30 ml of ethyl acetate and 30 ml of water were added, and the mixture was adjusted to basic using sodium bicarbonate. The organic layer was separated and the aqueous layer was further extracted with 10 ml×3 of ethyl acetate. The organic portion was washed once with saturated saline solution, dried over anhydrous magnesium sulfate and filtered, the solvent was evaporated to give 3.4 grams of ethyl 4-(1-hydroxy-1-methylethyl)-2-propyl-imidazole-5-carboxylate, resulting in a yield of 92%.

Example 4

The preparation of 4-(1-hydroxy-1-methylethyl)-2-propyl-imidazole-5-carboxylic acid (Formula III)

5.0 grams of 4,4-dimethyl-2-propyl-4,6-dihydrofuro[3,4-d]imidazole (formula II) from Example 1, 30 ml of acetone and 50 ml of 10% sodium hydroxide solution were added into 250 ml eggplant flask and refluxed until the reaction completed. Part of the solvent was removed by evaporation, and then the reactant was adjusted to acidic by dropwise addition of concentrated hydrochloric acid. The precipitation was filtered, collected and dried to give 5.3 grams of 4-(1-hydroxy-1-methylethyl)-2-propylimidazole-5-carboxylic acid (formula III), resulting in a yield of 96%.

$^1$H NMR (CDCl$_3$, 400 MHz): δ 2.60 (2H, triplet peak), 1.65 (2H, sextuplet peak), 1.48 (6H, singlet peak), 0.86 (3H, triplet peak); MS (Q-Tofmicro, ESI$^+$): 213.12 (M+1).

Example 5

The preparation of ethyl 4-(1-hydroxy-1-methylethyl)-2-propyl-imidazole-5-carboxylate (formula I, wherein R is ethyl)

3.0 grams of 4-(1-hydroxy-1-methylethyl)-2-propylimidazole-5-carboxylic acid (formula III) from Example 4, and 30 ml of ethanol were added into 100 ml three-necked flask, anhydrous hydrogen chloride gas was supplied while the temperature was maintained at 30-40° C. until the reaction completed. The reaction mixture was then allowed to cool to ambient temperature, the solvent was evaporated, 30 ml of ethyl acetate and 30 ml of water were added, and the mixture was adjusted to basic using sodium bicarbonate. The organic layer was separated and the aqueous layer was further extracted with 10 ml×3 of ethyl acetate. The organic portion was washed once with saturated saline solution, dried over anhydrous magnesium sulfate and filtered, the solvent was evaporated to give 2.8 grams of ethyl 4-(1-hydroxy-1-methylethyl)-2-propyl-imidazole-5-carboxylate, resulting in a yield of 82%.

Example 6

The preparation of ethyl 4-(1-hydroxy-1-methylethyl)-2-propyl-imidazole-5-carboxylate (formula I, wherein R is ethyl)

3.0 grams of 4-(1-hydroxy-1-methylethyl)-2-propylimidazole-5-carboxylic acid (formula III) from Example 4, 30 ml of ethanol, and 0.3 ml of concentrated sulfuric acid were added into 100 ml three-necked flask, and refluxed until the reaction completed. The reaction mixture was then allowed to cool to ambient temperature, the solvent was evaporated, 30 ml of ethyl acetate and 30 ml of water were added, and the mixture was adjusted to basic using sodium bicarbonate. The organic layer was separated and the aqueous layer was further extracted with 10 ml×3 of ethyl acetate. The organic portion was washed once with saturated saline solution, dried over anhydrous magnesium sulfate and filtered, the solvent was evaporated to give 2.5 grams of ethyl 4-(1-hydroxy-1-methylethyl)-2-propyl-imidazole-5-carboxylate, resulting in a yield of 74%.

Example 7

The preparation of ethyl 4-(1-hydroxy-1-methylethyl)-2-propyl-imidazole-5-carboxylate (formula I, wherein R is ethyl)

3.0 grams of 4-(1-hydroxy-1-methylethyl)-2-propylimidazole-5-carboxylic acid (formula III) from Example 4, 30 ml of ethanol, and 3.36 grams of thionyl chloride were added into 100 ml three-necked flask, and refluxed until the reaction completed. The reaction mixture was then allowed to cool to ambient temperature, the solvent was evaporated, 30 ml of ethyl acetate and 30 ml of water were added, and the mixture was adjusted to basic using sodium bicarbonate. The organic layer was separated and the aqueous layer was further extracted with 10 ml×3 of ethyl acetate. The organic portion was washed once with saturated saline solution, dried over anhydrous magnesium sulfate and filtered, the solvent was evaporated to give 2.9 grams of ethyl 4-(1-hydroxy-1-methylethyl)-2-propyl-imidazole-5-carboxylate, resulting in a yield of 85%.

Example 8

The preparation of methyl 4-(1-hydroxy-1-methylethyl)-2-propyl-imidazole-5-carboxylate (formula I, wherein R is methyl)

3.0 grams of 4,4-dimethyl-2-propyl-4,6-dihydrofuro[3,4-d]imidazole (formula II) from Example 1 and 30 ml of methanol were added into 100 ml three-necked flask and stirred until completely dissolved. Anhydrous hydrogen chloride gas was supplied while the temperature was maintained at 10-20° C. until the reaction completed. The reaction mixture was then allowed to cool to ambient temperature, the solvent was evaporated, 30 ml of ethyl acetate and 30 ml of water were added, and the mixture was adjusted to basic using sodium bicarbonate. The organic layer was separated and the aqueous layer was further extracted with 10 ml×3 of ethyl acetate. The organic portion was washed once with saturated saline solution, dried over anhydrous magnesium sulfate and filtered, the solvent was evaporated to give 2.1 grams of methyl 4-(1-hydroxy-1-methylethyl)-2-propylimidazole-5-carboxylate, resulting in a yield of 60%.

Example 9

The preparation of hexyl 4-(1-hydroxy-1-methyl-ethyl)-2-propyl-imidazole-5-carboxylate (formula I, wherein R is hexyl)

3.0 grams of 4,4-dimethyl-2-propyl-4,6-dihydrofuro[3,4-d]imidazole (formula II) from Example 1 and 30 ml of hexanol were added into 100 ml three-necked flask and stirred until completely dissolved. Anhydrous hydrogen chloride gas was supplied while the temperature was maintained at 10-20° C. until the reaction completed. The reaction mixture was then allowed to cool to ambient temperature, the solvent was evaporated, 30 ml of ethyl acetate and 30 ml of water were added, and the mixture was adjusted to basic using sodium bicarbonate. The organic layer was separated and the aqueous layer was further extracted with 10 ml×3 of ethyl acetate. The organic portion was washed once with saturated saline solution, dried over anhydrous magnesium sulfate and filtered, the solvent was evaporated to give 2.2 grams of hexyl 4-(1-hydroxy-1-methylethyl)-2-propyl-imidazole-5-carboxylate, resulting in a yield of 48%.

Example 10

The preparation of 4-(1-hydroxy-1-methylethyl)-2-propyl-imidazole-5-carboxylic acid (Formula III)

100 ml of 10% aqueous sodium hydroxide solution were added into a solution of 20 grams of ethyl 4-(1-hydroxy-1-methylethyl)-2-propyl-imidazole-5-carboxylate in 200 ml of acetone. The mixture was refluxed for 3 hours. After cooled to 10° C., pH of the reactant was adjusted to 6.4 using concentrated hydrochloric acid, solids precipitated. The precipitation was filtered, collected, washed with water, then dried to give 16.7 grams of whitish solid 4-(1-hydroxy-1-methylethyl)-2-propyl-imidazole-5-carboxylic acid (formula III), resulting in a yield of 95%.

Example 11

The preparation of 4,4-dimethyl-2-propyl-4,6-dihydrofuro[3,4-d]imidazole (formula II)

33.0 grams of dicyclohexylcarbodiimide (DCC) was added into a suspension of 30.0 grams of 4-(1-hydroxy-1-methylethyl)-2-propyl-imidazole-5-carboxylic acid (formula III) in 300 ml of acetone. The reaction was performed at ambient temperature for 48 hours. The mixture was suction filtered and washed. The filtrate was concentrated and acetone was recovered. 120 ml of ethyl acetate and 120 ml of water were added into the residual liquid, and pH was adjusted to 2-3 with concentrated hydrochloric acid. The aqueous layer was separated and the organic layer was further extracted with 20 ml×2 of water. 150 ml of ethyl acetate was added into the combined aqueous portion and pH was adjusted to 10 with 30% sodium hydroxide solution. Salt was added to be saturated and the organic layer was separated. The aqueous layer was further extracted with 30 ml×2 of ethyl acetate. Combined organic portion was dried over anhydrous magnesium sulfate and filtered, the solvent was evaporated to give 35.3 grams of 4,4-dimethyl-2-propyl-4,6-dihydrofuro[3,4-d]imidazole (formula II), resulting in a yield of 97%.

All cited documents in the present invention as cited throughout this application are hereby incorporated by reference as if each individual publication were individually indicated to be incorporated by reference. Moreover, person skilled in the art can, upon reading the disclosure in the present invention, readily modify and/or adapt for various applications, therefore, it is understood that such equivalents and alternatives also falling within the scope of the present invention as defined by the appended claims.

The invention claimed is:
1. A process for the preparation of compound of formula I,

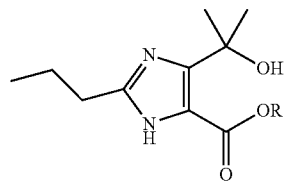

Formula I comprising mixing compound of formula II or formula III, with alcohol R—OH and a catalyst for transesterification or a condensation agent for oxygen acylation to produce compound of formula I,

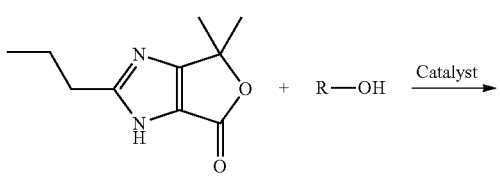

Formula II

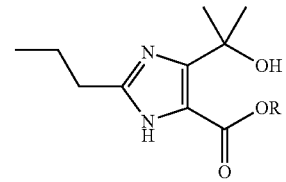

Formula I
or

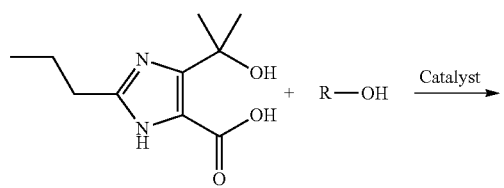

Formula III

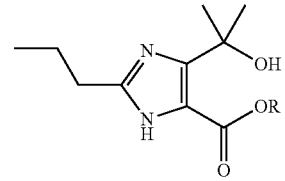

Formula I wherein R is selected from $C_1$-$C_6$ alkyl.

2. The process according to claim 1, wherein the reaction temperature is in the range of −20° C. to the reflux temperature of alcohol R—OH.

3. The process according to claim 1, wherein the reaction time is between 30 minutes and 72 hours.

4. The process according to claim 1, wherein the R is selected from $C_1$-$C_3$ alkyl.

5. The process according to claim 1, wherein the compound of formula III is produced by:

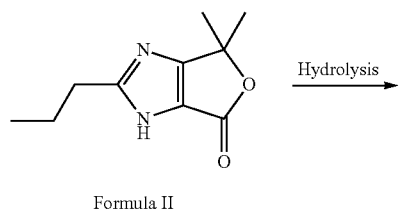

Formula II

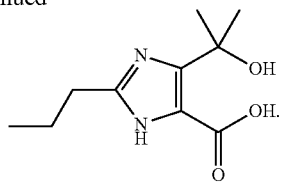

Formula III

6. The process according to claim 1, further comprising the following steps prior to the mixing step:
(1) hydrolyzing compound of formula V containing impurities 3 and/or 4 into compound of formula III, while impurities 3 and/or 4 being hydrolyzed into impurities 5 and/or 6;

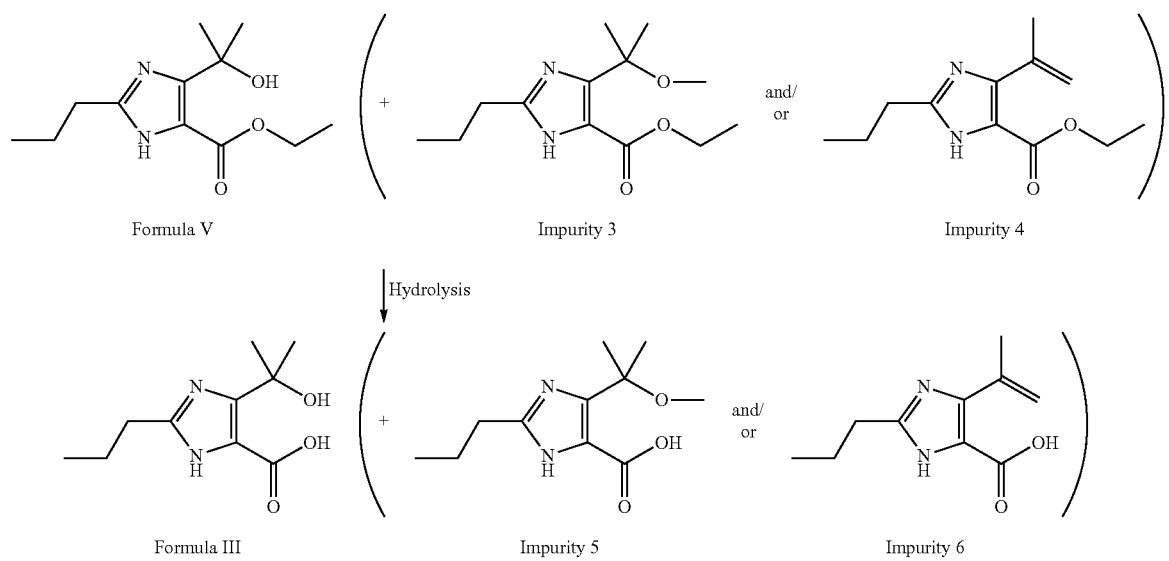

(2) mixing the compound of formula III with condensation agent in solvent to produce compound of formula II;

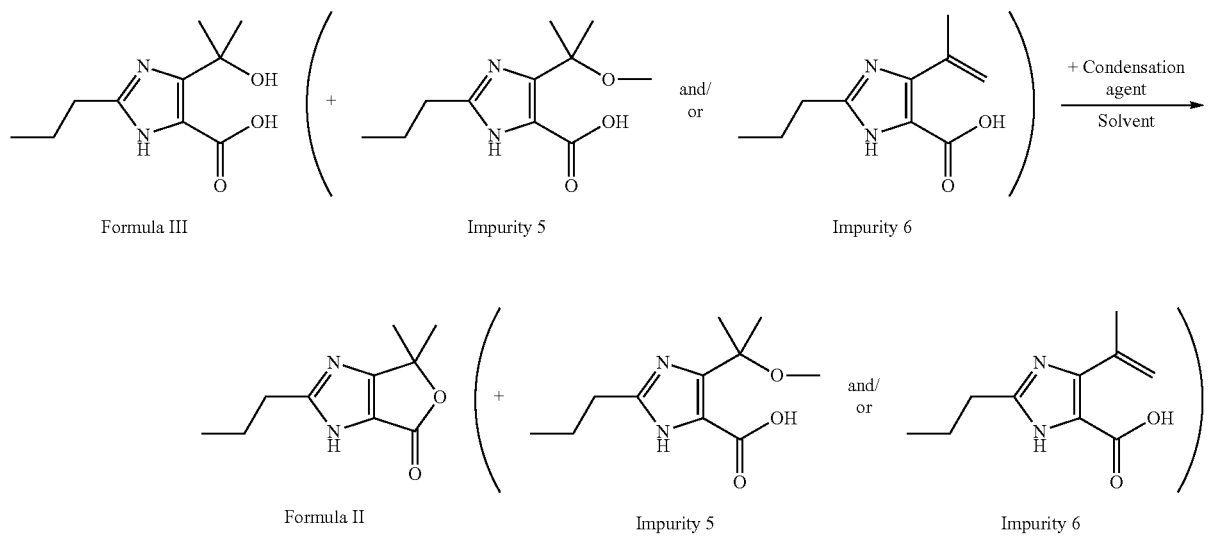

(3) mixing the compound of formula II with organic solvent and alkaline aqueous solution to remove salt of impurity 5 and/or salt of impurity 6 from the aqueous layer and collecting compound of formula II in the organic layer,

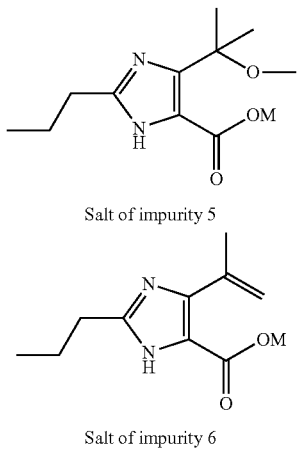

Salt of impurity 5

Salt of impurity 6 wherein M represents a group which can form water-soluble salts with carboxyl groups.

7. The process according to claim 6, further comprising following steps right after step (3):

(3') extracting the aqueous layer for 1-5 times with organic solvent; and/or (3") washing the organic layer with saturated saline solution for 1-5 times.

8. The process according to claim 6, wherein the condensation agent in step (2) is capable of catalyzing esterification.

9. The process according to claim 6, wherein the reaction temperature for step (2) is −20 to 100° C., and the reaction time is 1 to 56 hours.

10. The process according to claim 6, wherein M is an alkali metal.

11. The process according to claim 6, wherein the condensation agent in step (2) is capable of oxygen acylation.

12. The process according to claim 6, wherein the condensation agent in step (2) is a dehydrant for esterification.

* * * * *

UNITED STATES PATENT AND TRADEMARK OFFICE
CERTIFICATE OF CORRECTION

PATENT NO. : 8,618,308 B2  
APPLICATION NO. : 13/129686  
DATED : December 31, 2013  
INVENTOR(S) : Fuli Zhang et al.

Page 1 of 1

It is certified that error appears in the above-identified patent and that said Letters Patent is hereby corrected as shown below:

In the Claims:

1. Col. 16, Line 64, in claim 2, remove the "." between "-20°C" and "to"; and
2. Col. 20, Line 14, in claim 9, remove the "." between "100°C" and "and".

Signed and Sealed this  
Fourth Day of March, 2014

Michelle K. Lee  
*Deputy Director of the United States Patent and Trademark Office*